(12) United States Patent
Talanian et al.

(10) Patent No.: US 6,242,240 B1
(45) Date of Patent: Jun. 5, 2001

(54) MODIFIED INTERLEUKIN-1β CONVERTING ENZYME WITH INCREASED STABILITY

(75) Inventors: Robert V. Talanian, Harvard; John A. Mankovich, Andover; Tariq Ghayur, Grafton; Catherine R. Ferenz, Belchertown, all of MA (US)

(73) Assignee: BASF Aktiengellschaft, Ludwigshafen (DE)

( * ) Notice: Subject to any disclaimer, the term of this patent is extended or adjusted under 35 U.S.C. 154(b) by 0 days.

(21) Appl. No.: 09/248,179

(22) Filed: Feb. 9, 1999

Related U.S. Application Data

(63) Continuation of application No. 08/573,890, filed on Dec. 18, 1995, now Pat. No. 5,869,315.
(51) Int. Cl.$^7$ .............................. C12N 1/20; C12N 15/00; C12N 9/64; C07H 21/04
(52) U.S. Cl. ..................................... 435/252.3; 435/320.1; 435/226; 435/184; 435/219; 536/23.2; 536/23.5
(58) Field of Search ............................... 435/252.3, 320.1, 435/226, 184, 219; 536/23.2, 23.5

(56) References Cited

U.S. PATENT DOCUMENTS

| | | | |
|---|---|---|---|
| 5,416,013 | 5/1995 | Black et al. | 435/226 |
| 5,492,824 | 2/1996 | Talanian et al. | 435/226 |
| 5,869,315 | 2/1999 | Talanian et al. | 435/226 |

FOREIGN PATENT DOCUMENTS

| | | |
|---|---|---|
| WO 91/15577 | 10/1991 | (WO) . |
| WO 93/05071 | 3/1993 | (WO) . |
| WO 94/00154 | 1/1994 | (WO) . |
| WO 95/00160 | 1/1995 | (WO) . |

OTHER PUBLICATIONS

Alnemri, E.S. et al., "Cloning and expression of four novel isoforms of human interleukin–1β converting enzyme with different apoptotic activities", *J. Biol. Chem.*, vol. 270:9, pp. 4312–4317 (1995).

Black, R.A. et al., "Generation of biologically active interleukin–1β by proteolytic cleavage of the inactive precursor", *J. Biol. Chem.*, vol. 263:19, pp. 9437–9442 (1988).

Casano, F.J. et al., "The structure and complete nucleotide sequence of the murine gene encoding interleukin–1β converting enzyme (ICE)", *Genomics*, vol. 20, pp. 474–481 (1994).

Cerretti, D.P. et al., "Molecular cloning of the interleukin–1β Converting Enzyme", *Science*, vol. 256, pp. 97–100 (1992).

Faucheu, C. et al., "A novel human protease similar to the interleukin–1β converting enzyme induces apoptosis in transfected cells", *EMBO Journal*, vol. 14:9, pp. 1914–1922 (1995).

Fernandes–Alnemri, T. et al., "Mch2, a new member of the apoptotic Ced–3/Ice cysteine protease gene family", *Cancer Research*, vol. 55, pp. 2737–2742 (1995).

Fernandes–Alnemri, T. et al., "CPP32, a novel human apoptotic protein with homology to caenorhabditis elegans cell death protein Ced–3 and mammalian interleukin–1β–converting enzyme", *J. Biol. Chem.*, vol. 269:49, pp. 30761–30764 (1994).

Kamens, J. et al., "Identification and characterization of ICH–2, a novel member of the interleukin–1β–converting enzyme family of cysteine proteases", *J. Biol. Chem.*, vol. 270:25, pp. 15250–15256 (1995).

Kumar, S. et al., "Induction of apoptosis by the mouse Nedd2 gene, which encodes a protein similar to the product of the Caenorhabditis elegans cell death gene ced–3 and the mammalian IL–1β–converting enzyme", *Genes and Development*, vol. 8, pp. 1613–1626 (1994).

Malinowski et al., "Production purification, and crystallization of human interleukin–1β converting enzyme derived from an *Escherichia coli* expression system", *Protein Science*, vol. 4, pp. 2149–2155 (1995).

Molineaux, S.M. et al., "Interleukin 1β (IL–1β) processing in murine macrophages requires a structurally conserved homologue of human IL–1β converting enzyme", *Proc. Natl. Acad. Sci. USA*, vol. 90, pp. 1809–1813 (1993).

Munday, N.A. et al., "Molecular cloning and pro–apoptotic activity of ICE$_{rel}$II and ICE$_{rel}$II, members of the ICE/CED–3 family of xysteine proteases", *J. Biol. Chem.*, vol. 270:26, pp. 15870–15876 (1995).

Ramage et al., "Expression, Refolding, and Autocatalytic Proteolytic Processing of the Interleukin–1β–converting Enzyme Precursor", *The Journal of Biological Chemistry*, vol. 270, No. 16, Issue of Apr. 21, pp. 9378–9383, (1995).

Tewari, M. et al., "Yama/CPP32β, a mammalian homolog of CED–3, is a CrmA–inhibitable protease that cleaves the death substrate poly(ADP–ribose) polymerase", *Cell*, vol. 81, pp. 801–809 (1995).

(List continued on next page.)

*Primary Examiner*—Ponnathapu Achutamurthy
*Assistant Examiner*—Tekchand Saidha
(74) *Attorney, Agent, or Firm*—Lahive & Cockfield, LLP; Giulio A. DeConti, Jr.; Elizabeth A. Hanley

(57) ABSTRACT

Modified forms of human interleukin-1β converting enzyme (ICE) that display proteolytic activity and, furthermore, have increased stability compared to unmodified human ICE are disclosed. Nucleic acid molecules encoding a modified p10 subunit of ICE, and recombinant vectors and host cells incorporating such nucleic acid molecules, are also disclosed. A modified ICE protein of the invention can be used to cleave proteolytically ICE substrates and to identify modulators of ICE activity in screening assays. Moreover, due to its enhanced stability, the modified ICE of the invention is particularly suitable for use in the preparation of ICE crystals for X-ray crystallography.

15 Claims, 1 Drawing Sheet

OTHER PUBLICATIONS

Thornberry, N.A. et al., "A novel heterodimeric cysteine protease is required for interleukin–1β processing in monocytes", *Natue*, vol. 356, pp. 768–774 (1992).

Walker, N.P.C. et al., "Crystal structure of the cystein protease interleukin–1β–converting enzyme: a (p20/p10)$_2$ homodimer", *Cell*, vol. 78, pp. 343–352 (1994).

Wang L. et al., "Ich–1, an Ice/ced–3–related gene, encodes both positive and negative regulators of programmed cell death", *Cell*, vol. 78, pp. 739–750 (1994).

Wilson, K.P. et al., "Structure and mechanism of interleukin–1β converting enzyme", *Nature*, vol. 370, pp. 270–275 (1994).

Yuan, J. et al., "The C. elegans cell death gene ced–3 encodes a protein similar to mammalian interleukin–1β–converting enzyme", *Cell*, vol. 75, pp. 641–652 (1993).

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1216 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 1..1212

(xi) SEQUENCE DESCRIPTION: SEQ ID NO:1:

```
ATG GCC GAC AAG GTC CTG AAG GAG AAG AGA AAG CTG TTT ATC CGT TCC        48
Met Ala Asp Lys Val Leu Lys Glu Lys Arg Lys Leu Phe Ile Arg Ser
 1               5                  10                  15

ATG GGC GAA GGT ACA ATA AAT GGC TTA CTG GAT GAA TTA TTA CAG ACA        96
Met Gly Glu Gly Thr Ile Asn Gly Leu Leu Asp Glu Leu Leu Gln Thr
                20                  25                  30

AGG GTG CTG AAC AAG GAA GAG ATG GAG AAA GTA AAA CGT GAA AAT GCT       144
Arg Val Leu Asn Lys Glu Glu Met Glu Lys Val Lys Arg Glu Asn Ala
            35                  40                  45

ACA GTT ATG GAT AAG ACC CGA GCT TTG ATT GAC TCC GTT ATT CCG AAA       192
Thr Val Met Asp Lys Thr Arg Ala Leu Ile Asp Ser Val Ile Pro Lys
        50                  55                  60

GGG GCA CAG GCA TGC CAA ATT TGC ATC ACA TAC ATT TGT GAA GAA GAC       240
Gly Ala Gln Ala Cys Gln Ile Cys Ile Thr Tyr Ile Cys Glu Glu Asp
```

-continued

| | | | | | | | | | | | | | | | | |
|---|---|---|---|---|---|---|---|---|---|---|---|---|---|---|---|---|
| | 65 | | | | 70 | | | | 75 | | | | 80 | | | |
| AGT | TAC | CTG | GCA | GGG | ACG | CTG | GGA | CTC | TCA | GCA | GAT | CAA | ACA | TCT | GGA | 288 |
| Ser | Tyr | Leu | Ala | Gly | Thr | Leu | Gly | Leu | Ser | Ala | Asp | Gln | Thr | Ser | Gly | |
| | | | | 85 | | | | | 90 | | | | | 95 | | |
| AAT | TAC | CTT | AAT | ATG | CAA | GAC | TCT | CAA | GGA | GTA | CTT | TCT | TCC | TTT | CCA | 336 |
| Asn | Tyr | Leu | Asn | Met | Gln | Asp | Ser | Gln | Gly | Val | Leu | Ser | Ser | Phe | Pro | |
| | | | | 100 | | | | | 105 | | | | | 110 | | |
| GCT | CCT | CAG | GCA | GTG | CAG | GAC | AAC | CCA | GCT | ATG | CCC | ACA | TCC | TCA | GGC | 384 |
| Ala | Pro | Gln | Ala | Val | Gln | Asp | Asn | Pro | Ala | Met | Pro | Thr | Ser | Ser | Gly | |
| | | | 115 | | | | | 120 | | | | | 125 | | | |
| TCA | GAA | GGG | AAT | GTC | AAG | CTT | TGC | TCC | CTA | GAA | GAA | GCT | CAA | AGG | ATA | 432 |
| Ser | Glu | Gly | Asn | Val | Lys | Leu | Cys | Ser | Leu | Glu | Glu | Ala | Gln | Arg | Ile | |
| | | | 130 | | | | | 135 | | | | | 140 | | | |
| TGG | AAA | CAA | AAG | TCG | GCA | GAG | ATT | TAT | CCA | ATA | ATG | GAC | AAG | TCA | AGC | 480 |
| Trp | Lys | Gln | Lys | Ser | Ala | Glu | Ile | Tyr | Pro | Ile | Met | Asp | Lys | Ser | Ser | |
| 145 | | | | | 150 | | | | | 155 | | | | | 160 | |
| CGC | ACA | CGT | CTT | GCT | CTC | ATT | ATC | TGC | AAT | GAA | GAA | TTT | GAC | AGT | ATT | 528 |
| Arg | Thr | Arg | Leu | Ala | Leu | Ile | Ile | Cys | Asn | Glu | Glu | Phe | Asp | Ser | Ile | |
| | | | | 165 | | | | | 170 | | | | | 175 | | |
| CCT | AGA | AGA | ACT | GGA | GCT | GAG | GTT | GAC | ATC | ACA | GGC | ATG | ACA | ATG | CTG | 576 |
| Pro | Arg | Arg | Thr | Gly | Ala | Glu | Val | Asp | Ile | Thr | Gly | Met | Thr | Met | Leu | |
| | | | 180 | | | | | 185 | | | | | 190 | | | |
| CTA | CAA | AAT | CTG | GGG | TAC | AGC | GTA | GAT | GTG | AAA | AAA | AAT | CTC | ACT | GCT | 624 |
| Leu | Gln | Asn | Leu | Gly | Tyr | Ser | Val | Asp | Val | Lys | Lys | Asn | Leu | Thr | Ala | |
| | | | 195 | | | | | 200 | | | | | 205 | | | |
| TCG | GAC | ATG | ACT | ACA | GAG | CTG | GAG | GCA | TTT | GCA | CAC | CGC | CCA | GAG | CAC | 672 |
| Ser | Asp | Met | Thr | Thr | Glu | Leu | Glu | Ala | Phe | Ala | His | Arg | Pro | Glu | His | |
| | | 210 | | | | | 215 | | | | | 220 | | | | |
| AAG | ACC | TCT | GAC | AGC | ACG | TTC | CTG | GTG | TTC | ATG | TCT | CAT | GGT | ATT | CGG | 720 |
| Lys | Thr | Ser | Asp | Ser | Thr | Phe | Leu | Val | Phe | Met | Ser | His | Gly | Ile | Arg | |
| 225 | | | | | 230 | | | | | 235 | | | | | 240 | |
| GAA | GGC | ATT | TGT | GGG | AAG | AAA | CAC | TCT | GAG | CAA | GTC | CCA | GAT | ATA | CTA | 768 |
| Glu | Gly | Ile | Cys | Gly | Lys | Lys | His | Ser | Glu | Gln | Val | Pro | Asp | Ile | Leu | |
| | | | | 245 | | | | | 250 | | | | | 255 | | |
| CAA | CTC | AAT | GCA | ATC | TTT | AAC | ATG | TTG | AAT | ACC | AAG | AAC | TGC | CCA | AGT | 816 |
| Gln | Leu | Asn | Ala | Ile | Phe | Asn | Met | Leu | Asn | Thr | Lys | Asn | Cys | Pro | Ser | |
| | | | 260 | | | | | 265 | | | | | 270 | | | |
| TTG | AAG | GAC | AAA | CCG | AAG | GTG | ATC | ATC | ATC | CAG | GCC | TGC | CGT | GGT | GAC | 864 |
| Leu | Lys | Asp | Lys | Pro | Lys | Val | Ile | Ile | Ile | Gln | Ala | Cys | Arg | Gly | Asp | |
| | | | 275 | | | | | 280 | | | | | 285 | | | |
| AGC | CCT | GGT | GTG | GTG | TGG | TTT | AAA | GAT | TCA | GTA | GGA | GTT | TCT | GGA | AAC | 912 |
| Ser | Pro | Gly | Val | Val | Trp | Phe | Lys | Asp | Ser | Val | Gly | Val | Ser | Gly | Asn | |
| | | 290 | | | | | 295 | | | | | 300 | | | | |
| CTA | TCT | TTA | CCA | ACT | ACA | GAA | GAG | TTT | GAG | GAT | GAT | GCT | ATT | AAG | AAA | 960 |
| Leu | Ser | Leu | Pro | Thr | Thr | Glu | Glu | Phe | Glu | Asp | Asp | Ala | Ile | Lys | Lys | |
| 305 | | | | | 310 | | | | | 315 | | | | | 320 | |
| GCC | CAC | ATA | GAG | AAG | GAT | TTT | ATC | GCT | TTC | TGC | TCT | TCC | ACA | CCA | GAT | 1008 |
| Ala | His | Ile | Glu | Lys | Asp | Phe | Ile | Ala | Phe | Cys | Ser | Ser | Thr | Pro | Asp | |
| | | | | 325 | | | | | 330 | | | | | 335 | | |
| AAT | GTT | TCT | TGG | AGA | CAT | CCC | ACA | ATG | GGC | TCT | GTT | TTT | ATT | GGA | AGA | 1056 |
| Asn | Val | Ser | Trp | Arg | His | Pro | Thr | Met | Gly | Ser | Val | Phe | Ile | Gly | Arg | |
| | | | 340 | | | | | 345 | | | | | 350 | | | |
| CTC | ATT | GAA | CAT | ATG | CAA | GAA | TAT | GCC | TGT | TCC | TGT | GAT | GTG | GAG | GAA | 1104 |
| Leu | Ile | Glu | His | Met | Gln | Glu | Tyr | Ala | Cys | Ser | Cys | Asp | Val | Glu | Glu | |
| | | | 355 | | | | | 360 | | | | | 365 | | | |
| ATT | TTC | CGC | AAG | GTT | CGA | TTT | TCA | TTT | GAG | CAG | CCA | GAT | GGT | AGA | GCG | 1152 |
| Ile | Phe | Arg | Lys | Val | Arg | Phe | Ser | Phe | Glu | Gln | Pro | Asp | Gly | Arg | Ala | |
| | | | 370 | | | | | 375 | | | | | 380 | | | |
| CAG | ATG | CCC | ACC | ACT | GAA | AGA | GTG | ACT | TTG | ACA | AGA | TGT | TTC | TAC | CTC | 1200 |

```
Gln Met Pro Thr Thr Glu Arg Val Thr Leu Thr Arg Cys Phe Tyr Leu
385                 390                 395                 400

TTC CCA GGA CAT TAAA                                              1216
Phe Pro Gly His
```

(2) INFORMATION FOR SEQ ID NO:2:

(i) SEQUENCE CHARACTERISTICS:
        (A) LENGTH: 404 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Asp Lys Val Leu Lys Glu Lys Arg Lys Leu Phe Ile Arg Ser
1                   5                   10                  15

Met Gly Glu Gly Thr Ile Asn Gly Leu Leu Asp Glu Leu Leu Gln Thr
                20                  25                  30

Arg Val Leu Asn Lys Glu Glu Met Glu Lys Val Lys Arg Glu Asn Ala
            35                  40                  45

Thr Val Met Asp Lys Thr Arg Ala Leu Ile Asp Ser Val Ile Pro Lys
    50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Leu Ser Ser Phe Pro
            100                 105                 110

Ala Pro Gln Ala Val Gln Asp Asn Pro Ala Met Pro Thr Ser Ser Gly
        115                 120                 125

Ser Glu Gly Asn Val Lys Leu Cys Ser Leu Glu Glu Ala Gln Arg Ile
    130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
            180                 185                 190

Leu Gln Asn Leu Gly Tyr Ser Val Asp Val Lys Lys Asn Leu Thr Ala
        195                 200                 205

Ser Asp Met Thr Thr Glu Leu Glu Ala Phe Ala His Arg Pro Glu His
    210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
                245                 250                 255

Gln Leu Asn Ala Ile Phe Asn Met Leu Asn Thr Lys Asn Cys Pro Ser
            260                 265                 270

Leu Lys Asp Lys Pro Lys Val Ile Ile Ile Gln Ala Cys Arg Gly Asp
        275                 280                 285

Ser Pro Gly Val Val Trp Phe Lys Asp Ser Val Gly Val Ser Gly Asn
    290                 295                 300

Leu Ser Leu Pro Thr Thr Glu Glu Phe Glu Asp Asp Ala Ile Lys Lys
305                 310                 315                 320

Ala His Ile Glu Lys Asp Phe Ile Ala Phe Cys Ser Ser Thr Pro Asp
```

```
                325                 330                 335
Asn Val Ser Trp Arg His Pro Thr Met Gly Ser Val Phe Ile Gly Arg
            340                 345                 350
Leu Ile Glu His Met Gln Glu Tyr Ala Cys Ser Cys Asp Val Glu Glu
            355                 360                 365
Ile Phe Arg Lys Val Arg Phe Ser Phe Glu Gln Pro Asp Gly Arg Ala
            370                 375                 380
Gln Met Pro Thr Thr Glu Arg Val Thr Leu Thr Arg Cys Phe Tyr Leu
385                 390                 395                 400
Phe Pro Gly His
```

(2) INFORMATION FOR SEQ ID NO:3:

(i) SEQUENCE CHARACTERISTICS:
        (A) LENGTH: 57 bases
        (B) TYPE: nucleic acid
        (C) STRANDEDNESS: single
        (D) TOPOLOGY: linear (ii) MOLECULE TYPE: oligonucleotide primer (xi) SEQUENCE DESCRIPTION: SEQ ID NO:3:

```
GGGGAATTCA TGGCTATCAA AAAAGCTCAC ATCGAAAAAG ACTTCATCGC TTTCTGC          57
```

(2) INFORMATION FOR SEQ ID NO:4:

(i) SEQUENCE CHARACTERISTICS:
        (A) LENGTH: 42 bases
        (B) TYPE: nucleic acid
        (C) STRANDEDNESS: single
        (D) TOPOLOGY: linear (ii) MOLECULE TYPE: oligonucleotide primer (xi) SEQUENCE DESCRIPTION: SEQ ID NO:4:

```
TTCTGGCTGC TCAAATGAAA AACGAACCTT GCGGAAAATT TC                         42
```

(2) INFORMATION FOR SEQ ID NO:5:

(i) SEQUENCE CHARACTERISTICS:
        (A) LENGTH: 43 bases
        (B) TYPE: nucleic acid
        (C) STRANDEDNESS: single
        (D) TOPOLOGY: linear (ii) MOLECULE TYPE: oligonucleotide primer (xi) SEQUENCE DESCRIPTION: SEQ ID NO:5:

```
GGTTCGTTTT TCATTTGAGC AGCCAGAAGG TAGAGCGCAG ATG                        43
```

(2) INFORMATION FOR SEQ ID NO:6:

(i) SEQUENCE CHARACTERISTICS:
        (A) LENGTH: 35 bases
        (B) TYPE: nucleic acid
        (C) STRANDEDNESS: single
        (D) TOPOLOGY: linear (ii) MOLECULE TYPE: oligonucleotide primer (xi) SEQUENCE DESCRIPTION: SEQ ID NO:6:

```
CCCCACTAGT CCTCTATTAA TGTCCTGGGA AGAGG                                 35
```

MODIFIED INTERLEUKIN-1β CONVERTING ENZYME WITH INCREASED STABILITY

This application is a continuation application of Ser. No. 08/573,890 filed on Dec. 18, 1995, Issuing as U.S. Pat. No. 5,869,315. The contents of all of the aforementioned application(s) are hereby incorporated by reference.

BACKGROUND OF THE INVENTION

Interleukin-1 is a cytokine having a broad spectrum of biological activities (for reviews, see e.g., Dinarello, C. A. and Wolff, S. M. (1993) *New Engl. J. Med.* 328:106–113; and Dinarello, C. A. (1993) *Trends in Pharmacol. Sci.* 14:155–159). IL-1 consists of two structurally related polypeptides, interleukin-1α (IL-1α) and interleukin-1β (IL-1β). The two forms of IL-1 are encoded by different genes and have only 27–33% amino acid identity but they interact with the same receptor and have similar biological activities. Included among the biological functions attributed to IL-1 are induction of fever, sleep, anorexia and hypotension. IL-1 is also involved in the pathophysiology of inflammatory and autoimmune diseases, including rheumatoid arthritis, septic shock, inflammatory bowel disease and insulin dependent diabetes mellitus. IL-1α has been specifically implicated in the pathophysiology of psoriasis. IL-1 is also thought to play a role in immune responses to infectious agents and in the pathogenesis of myeloid leukemias.

IL-1α and IL-1β are both synthesized as approximately 31 kDa precursor molecules that are subsequently processed to a mature form of approximately 17 kDa. IL-1α and IL-1β differ in that the precursor form of IL-1α (preIL-1α) is biologically active and most of the mature IL-1α (matIL-1α) remains cell-associated, whereas the precursor form of IL-1β (preIL-1β) must be cleaved to its mature form to become active and the mature form of IL-1β (matIL-1β) is secreted from the cell. Only certain cell types process preIL-1β and secrete matIL-1β. Monocytes and macrophages are the most efficient producers and secretors of IL-1β, which is the most abundant form of IL-1 produced upon activation of these cell types.

Interleukin-1β converting enzyme (ICE) is a cytoplasmic cysteine protease required for generating the bioactive form of the interleukin-1β cytokine from its inactive precursor (Black, R. A. et al. (1988) *J. Biol. Chem.* 2:9437–9442; Kostura, M. J. et al (1989) *Proc. Natl. Acad. Sci. USA* 86:5227–5231; Thornberry et al. (1992) *Nature* 356:768–774; Ceretti, D. P. et al. (1992) *Science* 2:97–100). ICE is a member of a family of cysteine proteases with shared homology. Other members of this family have been implicated in apoptosis, such as ced-3 (Yuan, J. et al. (1993) *Cell* 75:641–652), Nedd2 (Kumar, S. et al. (1992) *Biochem. Biophys. Res. Commun.* 185:1155–1161; Kumar, S. et al. (1994) *Genes Dev.* 8:1613–1626), CPP32 (Femandes-Alnemri, T. et al. (1994) *J. Biol. Chem.* 269:30761–30764), Ich-1 (Wang, L. et al. (1994) *Cell* 78:739–750) and Ich-2 (Kamens, J. et al. (1995) *J. Biol Chem.* 270:15250–15256; Faucheu, C. et al. (1995) *EMBO J.* 14:1914–1922). The necessity for ICE in the generation of bioactive IL-1β was demonstrated in mice in which the ICE gene had been functionally disrupted (Li, P. et al. (1995) *Cell* 80:401–411; Kuida, K. et al. (1995) *Science* 267:2000–2003). Although these animals are overtly normal, they have a major defect in the production of mature IL-1β after stimulation with lipopolysaccharide.

In vitro studies have demonstrated that ICE cleaves prointerleukin-1β at $Asp_{116}$-$Ala_{117}$ to release the fully active 17 kDa form (Black, supra; Kostura, supra). ICE also cleaves prointerleukin-1β at $Asp_{27}$-$Ala_{28}$ to release a 28 kDa form. Cleavage at these sites is dependent upon the presence of aspartic acid in the P1 position (Kostura, supra, Howard, A. et al. (1991) *J. Immunol.* 147:2964–2969; Griffin, P. R. et al. (1991) *Int. J. Mass. Spectrom. Ion. Phys.* 111:131–149). However, an aspartic acid in the P1 position is not sufficient for ICE specificity. For example, several other proteins containing Asp-X bonds, including prointerleukin-1α, are not cleaved by ICE (Howard, supra).

ICE itself undergoes maturational processing, possibly performed in vivo by ICE itself (Thomberry, N. A. et al. (1992) *Nature* 3:768–774). Mature ICE is generated from a 404 amino acid precursor protein by proteolytic removal of two fragments, the N-terminal 119 amino acid "pro-domain" and the internal residues 298–316 (Thornberry, supra). Active ICE is therefore composed of two subunits, a 20 kDa subunit (p20) encompassing residues 120 to 297 and a 10 kDa subunit (p10) encompassing residues 317 to 404. The crystal structure of ICE indicates that ICE forms a tetrameric structure consisting of two p20 and two p10 subunits (Walker, N. P. C. et al. (1994), *Cell* 78:343–352; Wilson, K. P. et al. (1994) *Nature* 370:270–275). The catalytic amino acid residues of ICE are Cys-285 and His-237. The side chains of four amino acid residues (Arg-179, Gln-283, Arg-341 and Ser-347) form the P1 carboxylate binding pocket (Walker, supra; Wilson, supra).

Because of the apparently harmful role of IL-1 in many disease conditions, therapeutic strategies aimed at reducing the production or action of IL-1 have been proposed. For example, one approach by which to inhibit matIL-1β production and secretion would be to block the activity of ICE with a specific ICE inhibitor. The ability to produce active ICE in vitro is therefore highly desirable to allow for the study of its structure and function. However, in vitro production of ICE can be hampered by the instability of the protein, in particular as a result of autocatalytic degradation which leads to inactive protein.

SUMMARY OF THE INVENTION

This invention provides modified human ICE proteins that retain the proteolytic activity of unmodified human ICE and that exhibit increased stability in vitro compared to modified ICE. One aspect of the invention pertains to a modified form of ICE comprising an amino acid sequence wherein an amino acid corresponding to aspartic acid at position 381 of unmodified ICE (SEQ ID NO: 2) is replaced with a mutant amino acid structure. This mutant amino acid structure is one that is capable of forming a salt bridge with an amino acid corresponding to arginine at position 383 of unmodified ICE, such that the modified ICE exhibits proteolytic activity and has increased stability compared to unmodified ICE. The mutant amino acid structure that replaces the amino acid corresponding to Asp381 can be a natural amino acid or a non-natural amino acid. In the most preferred embodiment, the mutant amino acid structure is a glutamic acid residue. In other embodiments, the mutant amino acid structure is selected from the group consisting of serine, threonine, asparagine and glutamine.

Another aspect of the invention pertains to nucleic acid molecules encoding a modified p10 subunit of ICE. The modified p10 subunit encoded by the nucleic acid molecule comprises an amino acid sequence wherein an amino acid corresponding to aspartic acid at position 381 of unmodified ICE (SEQ ID NO: 2) is replaced with a mutant amino acid structure. The mutant amino acid structure is one that is capable of forming a salt bridge with an amino acid corresponding to arginine at position 383 of unmodified ICE, such that the modified p10 subunit associates with a p20 subunit to form a modified ICE that retains proteolytic activity and exhibits increased stability compared to unmodified ICE. In the most preferred embodiment, the p10 subunit encoded by the nucleic acid molecule has a glutamic acid residue at the position corresponding to position 381 of unmodified ICE. In other embodiments, the p10 subunit has a serine, threonine, asparagine or glutamine residue at the position corresponding to position 381 of unmodified ICE.

A nucleic acid molecule of the invention encoding a modified p10 subunit of ICE can be incorporated into a recombinant expression vector. In one embodiment, the recombinant expression vector encodes the modified p10 subunit of ICE (i.e., about amino acids 317 to 404). In another embodiment, the recombinant expression vector encodes the modified p10 subunit of ICE and also encodes the p20 subunit of ICE (i.e., about amino acids 120–197). For example, in one embodiment, the recombinant expression vector encodes the p30 form of ICE, comprising about amino acids 120–404. This p30 form of ICE undergoes maturational processing to produce a modified p10 subunit and a p20 subunit.

The recombinant expression vectors of the invention can be introduced into host cells to produce modified ICE proteins. In one embodiment, a modified p10 subunit is expressed recombinantly in a host cell, denatured and refolded with a p20 subunit of ICE to form a modified ICE protein of the invention. In another embodiment, a modified p10 subunit is coexpressed with a p20 subunit in the same host cell (using either two separate expression vectors or one expression vector encoding both the p10 and p20 subunits, such as a vector encoding p30), thereby producing a modified ICE protein of the invention.

The modified ICE proteins of the invention are cysteine proteases that exhibit proteolytic activity against ICE substrates. Accordingly, a modified ICE protein of the invention can be used to cleave an ICE substrate by contacting the ICE substrate with the modified ICE such that the ICE substrate is cleaved. Moreover, the modified ICE proteins of the invention can be used in screening assays to identify modulators (e.g., inhibitors or stimulators) of ICE protease activity. Still further, the enhanced stability of the modified ICE proteins of the invention makes them particularly well-suited for the preparation of crystalline ICE for use in X-ray cystallographic analysis (e.g., for structure-based design of ICE inhibitors).

DETAILED DESCRIPTION OF THE INVENTION

Figure 1:
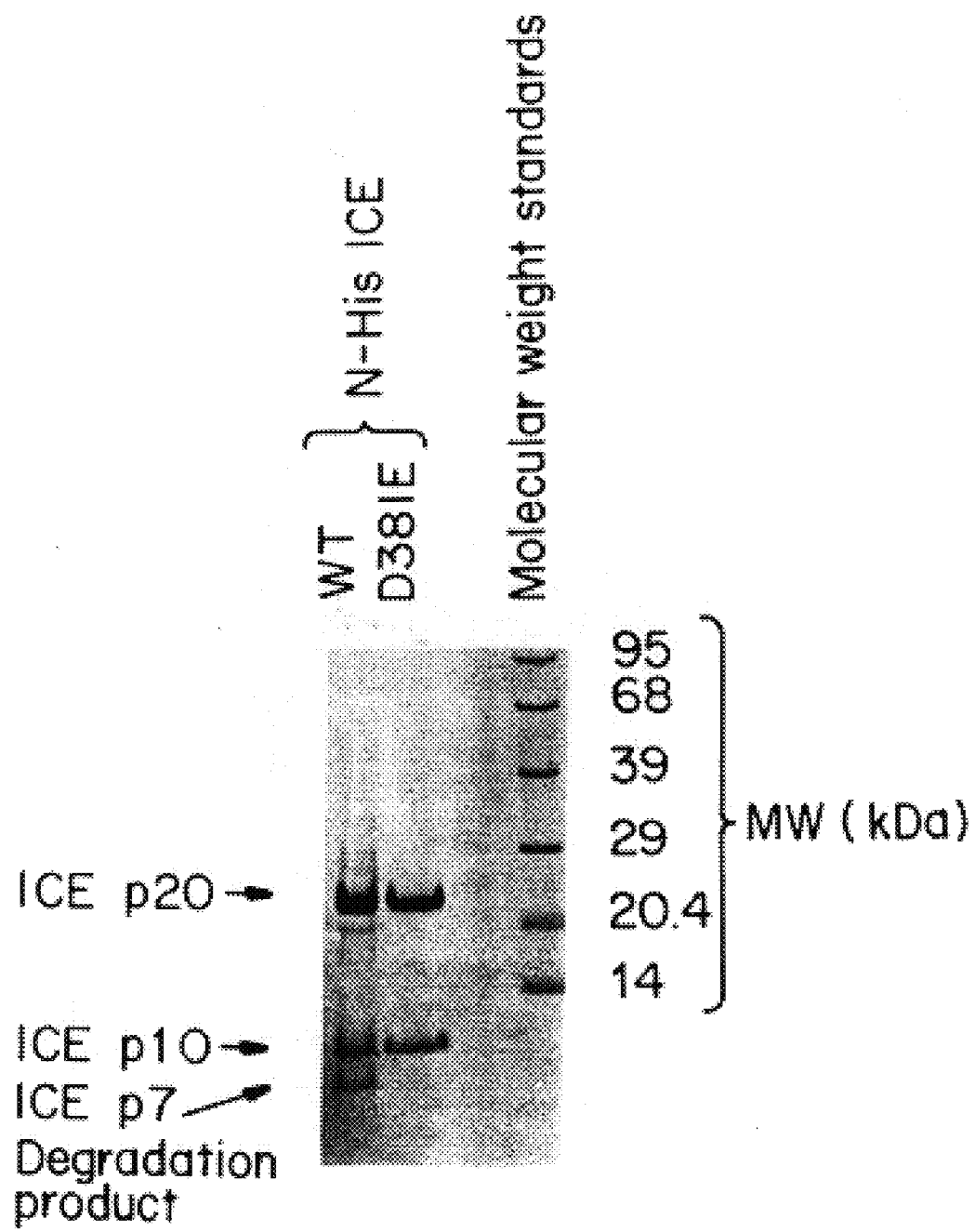
FIG. 1 is a photograph of an SDS-polyacrylamide gel comparing *E. coli*-expressed wild-type N-His ICE protein and *E. coli*-expressed D381E-modified N-His ICE protein.

This invention provides modified forms of human interleukin-1β converting enzyme (ICE) which retain the proteolytic activity of unmodified ICE yet also exhibit increased stability compared to unmodified human ICE. The invention is based, at least in part, on the discovery that mutation of ICE at an aspartic acid at position 381 (Asp-381) to glutamic acid (Glu-381) greatly increases the stability of the modified form of ICE (due to greatly reduced autocatalytic degradation of the protein), while maintaining the proteolytic activity of the protein. In contrast, it was further discovered that mutation of ICE at Asp-381 to alanine (Ala-381) results in a modified ICE protein that, although stable, exhibits greatly reduced proteolytic activity. These results were then applied to an analysis of the crystal structure of human ICE. The crystal structure of ICE demonstrated that Asp-381 forms a salt bridge with an arginine at position 383 (Arg-383). Since Glu-381 maintains this salt bridge and Ala-381 does not, preferred modifications in the modified ICE proteins of the invention are modifications at a position corresponding to Asp-381 that retain the capacity to form a salt bridge with an amino acid corresponding to Arg-383.

Various aspects of the invention are described in further detail in the following subsections.

I. Modified ICE Proteins

One aspect of the invention pertains to modified ICE proteins. As used herein, the term "unmodified ICE" refers to ICE proteins having the amino acid sequence of naturally-occurring human ICE. The term "unmodified ICE" includes the precursor form of ICE having the amino acid sequence shown in SEQ ID NO: 2 (the corresponding naturally-occurring nucleotide sequence that encodes unmodified human ICE is shown in SEQ ID NO: 1), as well as the processed mature form of ICE composed of p20 subunits (amino acids residues 120 to 297) and p10 subunits (amino acid residues 317 to 404). As used herein, the terms "aspartic acid at position 381 of unmodified ICE" (or simply Asp-381) and "arginine at position 383 of unmodified ICE" (or simply Arg-383) refer to amino acid residues within the p10 subunit using the numbering based on the full-length precursor form of ICE as shown in SEQ ID NO: 2.

As used herein, the term "modified ICE" refers to forms of ICE that differ structurally from unmodified ICE. In particular, the modified ICE proteins of the invention comprise an amino acid sequence wherein an amino acid corresponding to aspartic acid at position 381 of unmodified ICE (as shown in SEQ ID NO: 2) is replaced with a mutant amino acid structure, the mutant amino acid structure being capable of forming a salt bridge with an amino acid corresponding to arginine at position 383 of unmodified ICE. The mutant amino acid structure is selected such that the modified ICE retains proteolytic activity and exhibits increased stability compared to unmodified ICE. The term "mutant amino acid structure" is intended to include natural amino acids and non-natural amino acids. Non-natural amino acids include amino acid derivatives, analogues and mimetics. As used herein, a "derivative" of an amino acid refers to a form of the amino acid in which one or more reactive groups on the compound have been derivatized with a substituent group. As used herein an "analogue" of an amino acid refers to a compound that retains chemical structures of the amino acid necessary for functional activity of the amino acid (e.g., formation of a salt bridge with Arg-383 in ICE) yet also contains certain chemical structures that differ from the amino acid. As used herein, a "mimetic" of an amino acid refers to a compound in that mimics the chemical conformation of the amino acid.

Within the modified ICE proteins of the invention, an amino acid corresponding to aspartic acid at position 381 of unmodified ICE is replaced with a mutant amino acid structure that is capable of forming a salt bridge with an amino acid corresponding to arginine at position 383 of unmodified ICE. Mutant amino acid structures that are capable of forming a salt bridge with an amino acid corresponding to arginine at position 383 of unmodified ICE can be determined by computer modeling using the crystal structure of unmodified ICE (determination of the crystal structure of ICE is described in Walker, N. P. C. et al. (1994), *Cell* 78:343–352; and Wilson, K. P. et al. (1994) *Nature* 370:270–275). According to the crystal structure of unmodified ICE, Asp-381 forms a salt bridge with Arg-383. It has now been discovered that substitution of Asp-381 with glutamic acid, which retains the ability to form a salt bridge with Arg-383, results in a modified ICE that is both proteolytically active and more stable than unmodified ICE. In contrast, substitution of Asp-381 with an alanine, which cannot form a salt bridge with Arg-383, results in a modified ICE that, although stable, has lost proteolytic activity, thereby demonstrating the necessity for maintenance of this salt bridge for effective proteolytic activity.

In a modified ICE of the invention, Asp-381 of unmodified ICE is preferably substituted with another natural amino acid capable of forming a salt bridge with an amino acid corresponding to Arg-383. In the most preferred embodiment, Asp-381 is substituted with glutamic acid. In other embodiments, Asp-381 is substituted with an amino acid selected from the group consisting of serine, threonine, asparagine and glutamine. Other amino acids that can form a salt bridge with Arg-383 include derivatives of aspartic acid and glutamic acid, such as β-methylaspartic acid, γ-methylglutamic acid and β-methylglutamic acid, which may occur rarely in nature or which may be non-natural derivatives. Additional non-natural amino acids that can be used include analogues or mimetics of aspartic acid and glutamic acid that incorporate modifications into the peptide backbone of the ICE protein, such as an N-methyl aspartic acid or N-methyl glutamic acid. Moreover, a modified ICE protein of the invention can be modified at the amide linkage between Asp-381 and Gly-382, for example, the amide linkage can be substituted with an alkyl chain (thereby inhibiting proteolytic digestion at this linkage).

The modified ICE proteins of the invention exhibit increased stability compared to unmodified ICE. Preferably, the modified ICE protein is at least 10% more stable than unmodified ICE. More preferably, the modified ICE protein is at least 25% more stable than unmodified ICE. Even more preferably, the modified ICE is at least 50% more stable than unmodified ICE. Still more preferably, the modified ICE protein is at least 75% more stable than unmodified ICE. The stability of modified and unmodified ICE proteins can be examined and quantified by direct or indirect means. For example, the degree of degradation of modified or unmodified ICE can be assessed directly and used as a measure of the stability of the protein. The degree of degradation of an ICE preparation can be visualized directly by examining the protein by standard sodium dodecyl sulfate-polyacrylamide gel electrophoresis (SDS-PAGE). Samples containing a known amount of ICE protein (modified vs. unmodified) are electrophoresed on a standard SDS-PAGE gel and the protein bands are visualized by standard methods (e.g., Coomassie blue staining, silver staining and the like). Degradation of the ICE preparation is evidenced by the appearance of lower molecular weight breakdown products of the p10 subunit (i.e., protein band less than 10 kDa in weight, such as a predominant 7 kDa band), as described further in Example 2, part C and illustrated in FIG. 1. This degradation can be quantified by quantitating the relative amounts of protein in the intact p10 band as compared to the lower molecular weight bands in the ICE preparation. The relative amount of intact p10 in a modified ICE preparation is then compared to the relative amount of intact p10 in an unmodified ICE preparation as a measure of the stability of the modified ICE. For example, a modified ICE preparation in which the p10 band is 50% less degraded than in the unmodified ICE preparation represents a modified ICE protein that is 50% more stable than an unmodified ICE protein.

Alternatively, stability of the modified ICE proteins of the invention can be assessed indirectly, for example by measuring the proteolytic activity of modified vs. unmodified ICE preparations over time. A more stable ICE preparation exhibits greater proteolytic activity over time than a less stable ICE preparation (see Example 2, parts A and B). Proteolytic activity can be assessed in a standard in vitro proteolysis assay (such as described in Thornberry et al. (1992) *Nature* 3:768–774 and Example 2) using an appropriate ICE substrate. Examples of appropriate ICE substrates include the chromogenic para-nitroanilide (pNA)-labeled peptide substrates, Acetyl-Tyr-Val-Ala-Asp-pNA (Ac-YVAD-pNA) and Acetyl-Asp-Glu-Val-Asp-pNA (Ac-DEVD-pNA), and the fluorogenic amino-4-methylcoumarin (AMC)-labeled peptide substrates Acetyl-Tyr-Val-Ala-Asp-AMC (Ac-YVAD-AMC) and Acetyl-Asp-Glu-Val-Asp-pNA (Ac-DEVD-AMC). Ac-YVAD-pNA is described further in Reiter, L. A. (1994) *Int. J. Peptide Protein Res.* 43:87–96. Ac-YVAD-pNA and Ac-YVAD-AMC are commercially available from Bachem Bioscience, Inc., King of Prussia, PA. The rate constant of degradation of the modified ICE protein can be determined to quantitate the stability of the modified ICE protein.

Another aspect of the invention pertains to fusion proteins of the modified forms of ICE of the invention. The invention provides modified ICE proteins that are fusion proteins. As used herein the term "fusion protein" refers to a modified form of ICE in which non-ICE amino acid residues are fused at either the amino-terminus or carboxy-terminus. A preferred modified ICE fusion protein is one that has a polyhistidine tag (e.g, six histidine residues) at its amino terminus. This polyhistidine fusion moiety allows for purification of the modified ICE protein on a nickel chelating column (Porath, J. (1992) *Protein Expression and Purification* 2:263–281). Other fusion moieties can be used to facilitate protein purification, such as glutathione-S-transferase and maltose-binding protein. Preferably, a modified ICE fusion protein of the invention is prepared by recombinant DNA technology, as described further below.

II. Nucleic Acid Molecules Encoding Modified ICE Proteins

Another aspect of the invention pertains to nucleic acid molecules encoding the modified ICE proteins of the invention. The amino acid position that is modified in the ICE protein of the invention (i.e., position 381 of unmodified ICE), occurs within the p10 subunit of mature ICE. Accordingly, the invention provides a nucleic acid molecule encoding a modified p10 subunit of human ICE. This modified p10 subunit encoded by the nucleic acid comprises an amino acid sequence wherein an amino acid corresponding to aspartic acid at position 381 of unmodified ICE (SEQ ID NO: 2) is replaced with a mutant amino acid, the mutant amino acid being capable of forming a salt bridge with an amino acid corresponding to arginine at position 383 of unmodified ICE, such that the modified p10 subunit associates with a p20 subunit to form a modified ICE that retains proteolytic activity and exhibits increased stability compared to unmodified ICE. Most preferably, the nucleic acid molecule encodes a p10 subunit in which Asp-381 is replaced with glutamic acid. In other embodiments, the nucleic acid molecule encodes a p10 subunit in which Asp-381 is replaced with an amino acid selected from the group consisting of serine, threonine, asparagine and glutamine.

As used herein, the term "nucleic acid molecule" is intended to include DNA molecules and RNA molecules.

The nucleic acid molecule may be single-stranded or double-stranded, but preferably is double-stranded DNA.

The modified ICE proteins and nucleic acid molecules of the invention are preferably prepared using recombinant DNA technology. For example, to prepare a DNA fragment encoding a modified p10 subunit of ICE, first a DNA fragment encoding the region of unmodified ICE encompassing amino acid residues 317 to 404 (p10) is prepared, for example, by PCR amplification using appropriate primers designed using the nucleotide sequence of ICE shown in SEQ ID NO: 1. The oligonucleotide primers shown in SEQ ID NOs: 3 and 6 are suitable for amplifying a DNA fragment encoding an unmodified p10 subunit. The primer of SEQ ID NO: 3 corresponds to nucleotide sequences encoding the p10 amino terminus (starting at amino acid 317) and contains an EcoRI restriction site. The primer of SEQ ID NO: 6 is complementary to nucleotide sequences encoding the p10 carboxy terminus (amino acids 400–404) followed by a stop codon and includes an SpeI restriction site. The DNA fragment encoding the unmodified ICE p10 subunit can then be used as a template for mutagenesis to create a DNA fragment encoding a modified ICE p10 subunit. Mutagenesis can be accomplished by PCR mutagenesis (as described further in Example 1), or other standard methods known in the art such as site directed mutagenesis.

The nucleic acid molecules of the invention encoding modified ICE p10 subunits can be used to prepare modified ICE proteins of the invention. The nucleic acid molecules can be incorporated into recombinant expression vectors that allow for expression of the modified p10 subunit encoded therein. The modified p10 subunit can be expressed using an in vitro transcription/translation system or, more preferably, is expressed by introducing the recombinant expression vector into a suitable host cell in which the p10 subunit is then expressed (e.g., *E. coli*). A recombinant expression vector of the invention can encode only the modified p10 ICE subunit (i.e., about amino acids 317–404 of ICE). Alternatively, the recombinant expression can encode both the modified p10 subunit and a p20 subunit (e.g., a wild-type p20 subunit, comprising about amino acids 120–297 of ICE)). For example, in one embodiment of a recombinant expression vector encoding both the p10 and p20 subunits, the vector carries a DNA fragment encoding amino acids 120 to 404 of ICE (referred to as p30), wherein the amino acid corresponding to Asp-381 within the p10 subunit has been modified. The p30 fragment of ICE lacks the "pro-domain" from amino acids 1–119 but still contains the internal residues 298–316, which are cleaved from the precursor form of ICE to generate the p20 and p10 subunits. This p30 fragment is appropriately processed to p20 and p10 when expressed in a suitable host cell (e.g., *E. coli*). In yet another embodiment of a recombinant expression vector encoding both the p10 and p20 subunits, the vector encodes the entire precurser form of ICE (ie., amino acids 1–404), wherein the p10 subunit has been modified as described herein.

Accordingly, in one embodiment, a mature, active modified ICE protein of the invention is prepared by coexpression of p20 and p10 in a host cell (described further in Example 2, part B). The p20 and p10 subunits can be coexpressed in a host cell using a p30 encoding expression vector or, alternatively, by expression of separate p20 and p10 genes, either carried on the same vector or carried on two separate expression vectors. In another embodiment, a mature, active modified ICE protein of the invention is prepared by separately expressing the p20 and p10 subunits in different host cell, recovering the two subunits, denaturing them and renaturing the two subunits together to form mature, active ICE comprised of associated p20 and p10 subunits (described further in Example 2, part A).

III. Recombinant Expression Vectors

Another aspect of the invention pertains to vectors, preferably expression vectors, containing a nucleic acid encoding a modified ICE p10 subunit of the invention, alone or together with a p20 subunit. As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors, which serve equivalent functions.

In the recombinant expression vectors of the invention, ICE-encoding sequences are operatively linked to one or more regulatory sequences, selected on the basis of the host cells to be used for expression. The term "operably linked" is intended to mean that the ICE-encoding sequences are linked to the regulatory sequence(s) in a manner that allows for expression of ICE protein (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells thereby to produce proteins or peptides, including fusion proteins or peptides, encoded by nucleic acids as described herein.

The recombinant expression vectors of the invention can be designed for expression of modified ICE proteins in prokaryotic or eukaryotic cells. For example, modified ICE proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In a preferred embodiment, a DNA fragment encoding ICE p30 (amino acid residues 120–404) is cloned into an expression vector (e.g., an *E. coli* expression vector) that fuses a polyhistidine sequence (e.g., six histidine residues) to the N-terminus of the p30-coding sequence. The polyhistidine fusion moiety allows for purification of the mature ICE protein on a nickel chelating column (Porath, J. (1992) *Protein Expression and Purification* 2:263–281). Polyhistidine fusion expression vectors are commercially available (e.g., Novagen, Madison, Wis.).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn 10-lac fusion promoter mediated by a coexpressed viral RNA polymerase (T7 gn1). This viral polymerase is supplied by host strains BL21(DE3) or HMS 174(DE3) from a resident λ prophage harboring a T7 gn1 gene under the transcriptional control of the lacUV 5 promoter.

One strategy to maximize recombinant protein expression in *E. coli* is to express the protein in a host bacteria that is impaired in its capacity to cleave proteolytically the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Sharp and Li (1986) *Nucl. Acids Res.*, 14:7737–7749; Wada el al., (1992) *Nucl. Acids Res*. 20:2111–2118). Such alteration of nucleic acid sequences of the invention can be carried out by standard DNA synthesis techniques.

In another embodiment, the ICE expression vector is a yeast expression vector. Examples of vectors for expression in yeast *S. cerivisae* include pYepSec1 (Baldari et al., (1987) *EMBO J*. 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, ICE can be expressed in insect cells using baculovirus expression vectors. Baculovirus vectors available for expression of proteins in cultured insect cells (e.g., Sf9 cells) include the pAc series (Smith et al., (1983) *Mol Cell. Biol*. 3:2156–2165) and the pVL series (Lucklow, V. A., and Summers, M. D., (1989) *Virology* 170:31–39).

In yet another embodiment, a nucleic acid of the invention is expressed in mammalian cells using a mammalian expression vector. Examples of mammalian expression vectors include pCDM8 (Seed, B., (1987) *Nature* 329:840) and pMT2PC (Kaufman et al. (1987), *EMBO J*. 6:187–195). When used in mammalian cells, the expression vector's control functions are often provided by viral regulatory elements. For example, commonly used promoters are derived from polyoma, Adenovirus 2, cytomegalovirus and Simian Virus 40.

IV. Recombinant Host Cells

To prepare modified ICE proteins of the invention, typically one or more recombinant expression vectors are introduced into a suitable host cell in which the ICE protein is then expressed. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell may be any prokaryotic or eukaryotic cell. For example, modified ICE proteins may be expressed in bacterial cells such as *E. coli*, insect cells, yeast or mammalian cells. Preferably, modified ICE proteins are expressed in *E. coli* as described in the Examples.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those that confer resistance to drugs, such as G418, hygromycin and methotrexate. Nucleic acid encoding a selectable marker may be introduced into a host cell on the same vector as that encoding ICE protein or may be introduced on a separate vector. Cells stably transfected with the introduced nucleic acid can be identified by drug selection (e.g., cells that have incorporated the selectable marker gene will survive, while the other cells die).

V. Uses of Modified ICE Proteins

The modified ICE proteins of the invention retain the cysteine protease activity of unmodified ICE. Accordingly, the modified ICE proteins are useful as cysteine proteases.

Moreover, since a modified ICE protein of the invention has increased stability compared to unmodified ICE, a particular amount of this modified ICE protein exhibits greater proteolytic activity over time than an equal amount of unmodified ICE. Another aspect of the invention, therefore pertains to methods for cleaving ICE substrates. The method involves contacting the substrate with a modified ICE protein of the invention such that the ICE substrate is cleaved. The term "ICE substrate" is intended to include any peptide or protein which is cleavable by ICE. ICE substrates are characterized by an aspartic acid residue in the P1 position. Examples of ICE substrates include prointerleukin-1β, the chromogenic pNA-labeled peptide substrates Ac-YVAD-pNA and Ac-DEVD-pNA and the fluorogenic AMC-labeled peptide substrates Ac-YVAD-AMC and Ac-DEVD-AMC.

The modified ICE proteins of the invention can also be used in screening assays to identify modulators of ICE activity. The invention provides a method for identifying a modulator of ICE protease activity, comprising:

preparing a modified ICE protein of the invention;

contacting the modified ICE with an ICE substrate in the presence of a test compound under proteolytic conditions;

measuring proteolysis of the ICE substrate in the presence of the test compound;

comparing proteolysis of the ICE substrate in the presence of the test compound to proteolysis of the ICE substrate in the absence of the test compound; and identifying the test compound as a modulator of ICE protease activity.

In one embodiment, the modified ICE protein comprises an amino acid sequence wherein an amino acid corresponding to aspartic acid at position 381 of unmodified ICE (SEQ ID NO: 2) is replaced with a mutant amino acid structure, the mutant amino acid structure being capable of forming a salt bridge with an amino acid corresponding to arginine at position 383 of unmodified ICE, such that the modified ICE retains enzymatic activity and exhibits increased stability compared to unmodified ICE. In the most preferred embodiment, the mutant amino acid structure is glutamic acid. In other embodiments, the mutant amino acid structure is selected from the group consisting of serine, threonine, asparagine and glutamine.

In one embodiment of the screening method, an inhibitor of ICE protease activity is identified. In this case, the amount of proteolysis of the ICE substrate in the presence of the test compound is less than the amount of proteolysis of the ICE substrate in the absence of the test compound. In another embodiment of the screening method, an activator of ICE protease activity is identified. In this case, the amount of proteolysis of the ICE substrate in the presence of the test compound is greater than the amount of proteolysis of the ICE substrate in the absence of the test compound.

Suitable ICE substrates for use in the screening assays are described above. Preferably, a chromogenic or fluorogenic ICE substrate is used whose cleavage can be detected spectrophotometrically. Alternatively, cleavage of other peptide substrate can be detected chromatographically (e.g., by HPLC). Additionally, whole proteins can be used as substrates, such as prointerleukin-1β. Whole proteins can be labelled (e.g., with $^{35}$S-methionine) and their cleavage products can be directly detected (e.g., by SDS-PAGE and autoradiography). Alternatively, cleavage of whole proteins can be detected indirectly (e.g., using an antibody that binds a specific cleavage product).

In addition to the foregoing uses, the modified ICE proteins of the invention, because of their enhanced stability, are particularly well-suited for preparing crystalline ICE for X-ray crystallographic analysis. For example, unmodified ICE labeled at its N-terminus with a polyhistidine tag and expressed in E. coli was found to be too unstable (i.e., underwent too much autodegradation) to prepare crystals that could be used for X-ray crystallography. In contrast, D381E-modified ICE labeled at its N-terminus with a polyhistidine tag and expressed in E. coli was sufficiently stable for the preparation of crystals for X-ray crystallography. Accordingly, modified ICE proteins of the invention can be expressed recombinantly as described herein (e.g., in E. coli), the recombinant ICE protein can be purified and crystals can be prepared therefrom for use in X-ray crystallography. General methods for preparing crystalline ICE, and performing X-ray crystallographic analysis thereon, are described in Walker, N. P. C. et al. (1994) Cell 78:343–352 and Wilson, K. P. et al. (1994) Nature 370:270–275. Furthermore, a modified ICE protein of the invention can be used in X-ray crystallography in combination with a cysteine protease inhibitor, which serves to further stabilize the protein during crystallization, as described in U.S. Patent Application Serial No., entitled "Cysteine Protease Inhibitors and Uses Therefor", filed on even date herewith and expressly incorporated herein by reference.

This invention is further illustrated by the following examples which should not be construed as limiting. The contents of all references, patents and published patent applications cited throughout this application are hereby incorporated by reference.

EXAMPLE 1

Construction of a Modified ICE

A modified form of human ICE having an aspartic acid to glutamic acid substitution at amino acid position 381 (D381E) was constructed by polymerase chain reaction (PCR) mutagenesis of a DNA fragment encoding amino acids 317–404 of ICE (i.e., the p10 subunit) followed by in vivo recombination in E. coli.

PCR Amplification

To create a DNA fragment encoding p10 (amino acids 317–404) having a D381E mutation, two different DNA fragments were amplified by PCR that together represent the ICE 317–404 gene with a 28 base pair overlapping sequence (containing the mutation) where the two can be linked by homologous recombination in E. coli. Additionally, the DNA fragments were amplified such that they had restriction sites on each end for cloning into an expression vector.

For the first fragment (referred to as Fragment A), a plasmid encoding wild-type ICE 317–404 having a methionine start codon inserted before the ICE alanine-3 17 was used as the template. This open reading frame had its codons modified to reflect the preferred codon usage of highly expressed genes in E. coli, according to the codon usage information disclosed in Sharp and Li (1986) Nucl Acids Res., 14:7737–7749. The 5' primer (#694) had the following sequence: 5'-GGG GAA TTC ATG GCT ATC AAA AAA GCT CAC ATC GAA AAA GAC TTC ATC GCT TTC TGC-3' (SEQ ID NO: 3). This 5' primer is complementary to the ICE 317–404 amino terminus and contains an EcoRI restriction site. The 3' primer (#1537) had the following nucleotide sequence: 5'-TTC TGG CTG CTC AAA TGA AAA ACG AAC CTT GCG GAA AAT TTC-3' (SEQ ID NO: 4). This 3' primer contains nucleotide sequences encoding the amino acid region ICE 368–381 and contains 2 mutations. The first is an A to T point mutation at the 5' end (position 1) of the oligonucleotide that changes aspartic acid-381 to glutamic acid. The second is a silent point mutation (T to A at position 22 of the oligo) that eliminates a TaqI site to be used for clone screening but does not further change the amino acid sequence of the encoded p10 subunit. PCR amplification using these two primers and the wildtype ICE 317–404 containing plasmid as template resulted in a fragment containing an open reading frame encoding ICE 317–381 having the D381E mutation, with an EcoRI site for cloning at the 5' end.

For the second fragment (referred to as Fragment B), the template was the same as the first. The PCR reaction utilized a 5' primer (#1533) having the nucleotide sequence: 5'-GGT TCG TTT TTC ATT TGA GCA GCC AGA AGG TAG AGC GCA GAT G-3' (SEQ ID NO: 5). This 5' primer contains nucleotide sequences encoding the amino acid region ICE 373–386 and contains the complements to the 2 mutations described in the previous paragraph. The PCR reaction utilized a 3' primer (#518) having the following sequence: 5'-CCC CAC TAG TCC TCT ATT AAT GTC CTG GGA AGA GG-3' (SEQ ID NO: 6). The 3' primer contains nucleotide sequences encoding the amino acid region ICE 400–404 followed by a stop codon and includes an SpeI restriction site. PCR amplification using these primers and the plasmid encoding wild-type ICE 317–404 as template resulted in a fragment containing an open reading frame encoding ICE 373–404, including the D381E mutation, followed at the 3' end by the SpeI restriction site for cloning into the expression vector.

Standard PCR conditions were used to obtain the PCR fragments described above using 30 cycles of 94° C. denaturing step for 30 seconds, annealing for 30 seconds at 52° C., and 2 minutes elongation at 72° C. These 30 cycles were followed by 5 minutes at 73° C. for final extension. The reactions were then held at 4° C. until ready for further use. Five microliters of each of the appropriate primers at 20 $\mu$M concentrations were used in each reaction with the following additional reaction components: 1 $\mu$l of template DNA at 1 $\mu$g/ml, 10 $\mu$l of standard 10×PCR buffer containing $MgCl_2$ (PE Express, Norwalk, Conn.), 8 $\mu$l of dNTP mix containing 2.5 mM each of deoxynucleotide triphosphate (PE Express, Norwalk, Conn.), 0.5 $\mu$l Taq polymerase (PE Express, Norwalk, Conn.) and 70 $\mu$l of deionized $dH_2O$ for a final volume of 100 $\mu$l.

10 $\mu$l each of the two PCR fragments, Fragments A and B, from the two PCR reactions described above, were then separately run out on 1% agarose gels (FMC Bioproducts, Rockland, Me.) containing 0.5 $\mu$g/ml ethidium bromide to visualize the resultant bands under UV Light. Both PCR products were observed, Fragment A at 206 base pairs and Fragment B at 114 base pairs. The remaining PCR mix was extracted with an equal volume of phenol:chloroform:isoamyl alcohol (25:24:1 v/v). The aqueous phase was brought to 1M $LiCl_2$ and the DNA was precipitated by the addition of 3 volumes of 100% ethanol The DNA was collected by centrifugation. The pellet was washed with 70% ethanol, recentrifuged and dried under vacuum. The ends of the fragments were digested with EcoRI (fragment A) or SpeI (fragment B) in 50 $\mu$l reactions containing appropriate reaction buffer and 20 units of restriction enzyme. The reactions were allowed to proceed at 37° C. overnight.

Following restriction enzyme digestion, Fragments A and B were then separately electrophoresed on 4% Metaphor agarose gels (FMC Bioproducts, Rockland, Me.) containing 0.5 $\mu$g/ml ethidium bromide to visualize the resultant bands under UV light. The expected size bands were observed and purified by electrophoresis onto DEAE paper for 10 minutes at 100 V and eluted with buffer containing 20% ethanol, 1 M $LiCl_2$, 10 mM tris pH 7.5, and 1 mM EDTA. The eluate was then precipitated with isopropanol, pelleted, washed with 70% ethanol, dried by speed vacuum and resuspended in 10 $\mu$l 10 mM tris, 1 mM EDTA pH 8.0.

Ligation of Fragments A and B to Expression Vector

The two PCR fragments (A and B) were ligated to the ends of the linearized expression vector pJAM-4. pJAM-4 is a derivative of pBluescript II KS(+) (Stratagene, La Jolla, Calif.) consisting of the bacteriophage Larnbda left promoter (pL) followed by a ribosome binding site which is in turn followed by a polylinker sequence starting with an EcoRI site. The vector also carries an anpicillin resistance gene, the ColE1 origin and the f1 (+) origin.

The expression vector pJAM-4 (10 $\mu$g) was digested with EcoRI and SpeI by standard methods. The linearized vector was purified from a 1% agarose gel containing 0.5 $\mu$g/ml ethidium bromide using DEAE paper, as described above. The linearized vector was resuspended to an estimated concentration of 500 ng/$\mu$l in $dH_2O$.

A ligation reaction was prepared containing the following reaction components: 5 $\mu$l each of fragments A and B, 1 $\mu$l of linearized pJAM-4, 2 $\mu$l 10×Ligase buffer (New England Biolabs, Beverly, Mass.), 1 $\mu$l T4 DNA Ligase (400 units) (New England Biolabs, Beverly, Mass.) and 6 $\mu$l $dH_2O$. Ligation was carried out overnight at 16° C. Following the ligation reaction, the ligation mix was extracted with phenol:chloroform:isoamyl alcohol (25:24:1 v/v) and precipitated as described above. The resulting DNA pellet was dissolved in a final volume of 10 $\mu$l $dH_2O$.

Following the precipitation, the ligation products were transformed into competent *E. coli* strain MV1190 (Δ(lac-proAB), thi, supE, Δ(srl-recA) 306::Tn10(Tet$^r$) [F':traD36, proAB, lacI$^q$lacZΔM15]) (Bio-Rad Laboratories, Hercules, Calif.) carrying plasmid pSE103. pSE103 is a kanamycin resistant pSC101 derivative carrying the temperature sensitive bacteriophage Lambda repressor, cI$^{857}$. Competent MV1190 pSE103 cells were prepared as follows: A 3 ml seed culture in 2×YT media (Sambrook, J. et al. (1989) *Molecular Cloning: A Laboratory Manual*, Cold Spring Harbor, N.Y.:Cold Spring Harbor Press) was grown overnight at 30° C. from a frozen seed culture in the presence of 50 $\mu$g/ml kanamycin. The overnight culture was used to inoculate a larger culture (100–250 ml of 2×YT containing 50 $\mu$g/ml kanarnycin) using a 1/50 dilution of the seed culture. The cells were grown with shaking at 30° C. until the $OD_{600}$ value reached 0.5. Cells were harvested by low speed centrifigation, the cell pellet was resuspended in ½ original volume of ice cold 10 mM $MgCl_2$, 30 mM $CaCl_2$, 10% glycerol and the suspension allowed to sit on ice for 30 minutes. The cells were recentrifuged at low speed and the cell pellet was resuspended in 1/10 the original culture volume of the same solution above. The competent cells were dispensed into 100 $\mu$l aliquots and stored at −80° C. until use.

The cells were transformed using the linear DNA that resulted from the ligation of fragments A and B to the ends of the vector DNA, as follows. In a pre-chilled tube, 5 $\mu$l of ligation mix was added to 100 $\mu$l of competent MV1190 pSE103 cells and incubated on ice for 30 minutes. The mixture was heat shocked at 37° C. for 2 minutes, then added to 1 ml 2×YT medium and incubated for 1 hour at 30° C. 100 $\mu$l of the medium was plated onto Luria-Bertani (LB) plates (ampicillin, 100 $\mu$g/ml; kanamycin, 50 $\mu$g/ml) (Sambrook, et al., supra) and incubated at 30° C. overnight. The linear DNA, once inside the cell, undergoes a recA-independent recombination event by virtue of the 28 base pair overlapping sequences of Fragment A and Fragment B.

This results in the recovery of an intact gene inserted into the expression vector which encodes p10 (amino acids 317–404) having the D381E mutation.
Identification of Positive Clones Transformants were screened by restriction enzyme digestion of plasmid DNA minipreps. The enzymes used were EcoRI and HindIII. Transformants containing inserts of the correct size were used to prepare larger amounts of pure plasmid for further analysis. The presence of the D381E mutation was demonstrated by detecting the linked mutation which resulted in the destruction of a TaqI site (by TaqI digests) and by complete nucleotide sequence determination of the insert.
Expression of ICE 317–404 D381E Expression of the mutant p10 subunit (ICE 317–404 D381E) was carried out in the protease-deficient *E. coli* strain CAG 597 (F-;rpoH165(am) zhg::Tn10 lacZ(am) trp (am) pho(am) supCts mal(am) rpsL) (New England Biolabs, Beverly, Mass.) containing pACYC 177cI$^{857}$ (Kanamycin$^R$). The p10 expression plasmid pJAM-4 ICE 317–404 D381E was transformed into the bacterial cells as described above. Transformants were selected on Luria-Bertani (LB) plates (arnpicillin, 100 μg/ml; kanamycin, 50 μg/ml) (Sambrook, et al., supra) and incubated at 30° C. overnight. A single colony was used to inoculate a 3 ml 2×YT (ampicillin, 100 μg/ml; kanamycin, 50 μg/ml) culture and incubated at 30° C. overnight. One liter of 2×YT (ampicillin, 100 μg/ml; kanamycin, 50 μg/ml) was inoculated with 0.5 ml of overnight seed culture and incubated approximately 4 hours at 30° C. with shaking. Expression of the mutant p10 was induced by shifting the incubator temperature to 42° C. and the induced culture was incubated an additional 4 hours to allow for protein production. The cells were harvested by centrifugation and the pellets stored at –80° C. until ready for use.

EXAMPLE 2

Relative Activity and Stability of D381E-Modified ICE Compared to Unmodified ICE The D381E-modified form of ICE was prepared in two ways and its activity and/or stability was compared to wild-type (WT) ICE (i.e., unmodified ICE). First, unmodified and D381E-modified ICE were prepared by refolding separately-expressed p20 (WT) and p10 (WT or D381B mutant) subunits thereby to produce active, mature ICE (p20/p10). Second, unmodified and D381E-modified ICE were prepared by expression in bacteria of a single protein (p30) that encompasses both p20 and p10, and that autoproteolytically processes to the active, p20/p10 form (either fully WT or containing a p10 subunit carrying the D381E mutation). The p30-encoding constructs also contained an amino terminal poly-Histidine tag to allow for rapid purification of the protein, and are referred to as WT N-His ICE (for wild-type) and D381E N-His ICE (for the D381E mutant).
A. Comparative Activity of WT and D381E-Modified ICE Refolded From p20 and p10 Subunits ICE (WT or modified) was prepared by refolding p20 and p10, which had been separately expressed in *E. coli*, by a protocol described in U.S. patent application Ser. No. 08/242,663, entitled "ICE and ICE-Like Compositions and Methods of Making Same", which is expressly incorporated herein by reference. The p20 subunit was prepared by HPLC purification of material expressed as inclusion bodies in *E. coli*. The p10 subunit (either wild-type, the D381A-modified form or the D381E-modified form) was used only as crude inclusion bodies. A control of HPLC-purified wild-type p10 was also included to estimate the effect on the system of the crude inclusion bodies, but the conclusions of the experiment were derived from the comparison of the three crude materials.

During the final step of the refolding protocol, which consists of dialysis from a tris buffer into a HEPES buffer, ICE proteolytic activity against an ICE substrate develops gradually over a few hours. ICE activity was monitored as a function of time in the HEPES dialysis. Four samples, each differing in the p10 species used, were compared: HPLC-pure wild-type, crude wild-type, crude D381A, and crude D381E. The results of this experiment are shown below in Table I, wherein ICE activity is expressed in arbitrary units.

TABLE I

| Time into HEPES dialysis | Pure WT | Crude WT | Crude D381A | Crude D381E |
|---|---|---|---|---|
| 0 hours | 879 | 95 | 28 | 370 |
| 2 hours | 2165 | 1200 | 237 | 3246 |
| 2.5 hours | 4609 | 1332 | 220 | 3316 |
| 3.5 hours | 4789 | 1082 | 252 | 3976 |
| 4 hours | 5228 | 1276 | n.d. | 3832 |
| 4.5 hours | 4988 | n.d. | n.d. | 3524 |
| 5 hours | 5112 | 1356 | 584 | 4030 | n.d. = not done

These results demonstrate that the D381E mutation produces a modified form of ICE with a final yield and/or specific activity that is equal to or greater than that of unmodified ICE. In contrast, the D381A mutation produces a modified form of ICE with substantially lower catalytic activity than that of unmodified ICE.
B. Comparative Activity of Wild-Type and D381E-Modified N-His ICE:

ICE (WT or modified) with an N-terminal polyhistidine tag was expressed in *E. coli* and purified using methodology described in Kamens et al. (1995) *J. Biol. Chem.*, 270:15250–15256. Briefly, a DNA fragment encoding amino acid residues 120 to 404 of wild-type or D381E-modified ICE (p30) was cloned into an expression vector such that the p30-encoding fragment was fused in-frame at its N-terminus to DNA encoding six histidine residues. Following expression, the p30 fragment is correctly processed to p20 and p10 subunits, which associate to form mature, active N-His-tagged ICE proteins. The N-His ICE fusion proteins then were purified on a nickel chelating column (Porath, J. (1992) *Protein Expression and Purification* 2:263–281).

The proteolytic activity of nickel-column-purified WT and D381E-modified ICE was examined using two pNA-labeled substrates, Ac-YVAD-pNA and Ac-DEVD-pNA. To perform the proteolysis assay, modified or unmodified N-His ICE was preincubated for 60 minutes at 30° C. in 80 μl of a reaction buffer containing 100 mM HEPES, 20% (v/v) glycerol, 5 mM DTT, 0.5 mM EDTA, at pH 7.5. The peptide substrate was added in 20 μl of reaction buffer containing 2.5 mM substrate and 5% DMSO solvent, giving final concentrations in the assay mixtures of 500 μM substrate and 1% DMSO. The incubation of N-His ICE with the peptide substrate at 30° C. was continued, and the catalytic hydrolysis of peptide substrate was monitored by the change in absorbance of the samples at 405 nm due to release of pNA as a function of time. Assays were performed in duplicate. Samples were read using a microtiter plate reader (Molecular Devices, Sunnyvale, Calif.).

The Michaelis-Menten Km and Vmax values for the unmodified and modified N-His ICE using the two peptide substrates were determined by standard methods. The results are shown below:

|  | D381E | WT |
|---|---|---|
|  | $K_m$ values ($\mu M$) |  |
| Ac-YVAD-pNA | 43 | 26 |
| Ac-DEVD-pNA | 44 | 25 |
|  | $V_{max}$ values ($M^{-1}\ s^{-1}$) |  |
| Ac-YVAD-pNA | 0.19 | 0.04 |
| Ac-DEVD-pNA | 0.08 | 0.02 |

The similarities in the Km values for both substrates between the two enzymes demonstrate that WT and D381E-modified ICE are functionally similar. That the Vmax values are substantially greater with the D381E form for both substrates, as compared to the WT form, most likely reflects the fact that a large fraction of the WT enzyme is degraded and therefore inactive.

C. Visualization/Quantitation of Increased Stability of D381E N-His ICE

To confirm that D381E-modified N-His ICE was more stable (i.e., underwent less autocatalytic degradation) than WT N-His ICE, as suggested in part B above, nickel column purified material (WT or D381E) was analyzed by standard SDS-polyacrylamide electrophoresis. Representative results are shown in FIG. 1. The WT N-His ICE preparation consisted of the expected p20 and p10 bands as well as smaller molecular weight breakdown products, the most visible being a p7 band in FIG. 1. By sequencing analysis, this p7 band has been identified as the larger cleavage product that results from cleavage of p10 at Asp-381/Gly-382. Although not visible in FIG. 1, a p3 band, corresponding to the smaller cleavage product that results from cleavage of p10 at Asp-281/Gly-382, has also been identified in the WT N-His ICE preparation. In contrast to the WT preparation, these lower molecular weight breakdown products are not detectable in the D381E N-His ICE preparation shown in FIG. 1, whereas the p20 and p10 subunits are readily detectable. The degree of degradation of p10 in the WT material is estimated to be at least 50% compared to the modified material. This high degree of degradation of the WT sample rendered it unsuitable for use in crystallography. In contrast, the D381E-modified material, which had no discernible degradation of p10, was used successfully to form crystals that diffract to high resolution for X-ray crystallographic analysis of the ICE structure.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. A nucleic acid molecule encoding a modified p10 subunit of interleukin-1β converting enzyme (ICE), the modified p10 subunit comprising an amino acid sequence wherein an amino acid corresponding to aspartic acid at position 381 of unmodified ICE (SEQ ID NO: 2) is replaced with a mutant amino acid structure, the mutant amino acid structure being capable of forming a salt bridge with an amino acid corresponding to arginine at position 383 of unmodified ICE, such that the modified p10 subunit associates with a p20 subunit to form a modified ICE which retains proteolytic activity and exhibits increased stability compared to unmodified ICE.

2. A recombinant expression vector comprising the nucleic acid molecule of claim 1.

3. The recombinant expression vector of claim 2, which further encodes a p20 subunit of ICE.

4. A host cell containing the recombinant expression vector of claim 2.

5. A host cell containing the recombinant expression vector of claim 3.

6. A nucleic acid molecule encoding a modified p10 subunit of interleukin-1β converting enzyme (ICE), the modified p10 subunit comprising an amino acid sequence wherein an amino acid corresponding to aspartic acid at position 381 of unmodified ICE (SEQ ID NO: 2) is replaced with glutamic acid.

7. A recombinant expression vector comprising the nucleic acid molecule of claim 6.

8. The recombinant expression vector of claim 7, which further encodes a p20 subunit of ICE.

9. A host cell containing the recombinant expression vector of claim 7.

10. A host cell containing the recombinant expression vector of claim 8.

11. A nucleic acid molecule encoding a modified p10 subunit of interleukin-1β converting enzyme (ICE), the modified p10 subunit comprising an amino acid sequence wherein an amino acid corresponding to aspartic acid at position 381 of unmodified ICE (SEQ ID NO: 2) is replaced with an amino acid selected from the group consisting of serine, threonine, asparagine and glutamine.

12. A recombinant expression vector comprising the nucleic acid molecule of claim 11.

13. The recombinant expression vector of claim 12, which further encodes a p20 subunit of ICE.

14. A host cell containing the recombinant expression vector of claim 12.

15. A host cell containing the recombinant expression vector of claim 13.

* * * * *